United States Patent [19]  
Lim et al.

[11] Patent Number: 4,799,934  
[45] Date of Patent: Jan. 24, 1989

[54] SULFUR-CONTAINING NITROAMINOBENZENE DYES, PROCESS AND HAIR DYE COMPOSITIONS

[75] Inventors: Mu-Ill Lim, Trumbull; James S. Anderson, Danbury, both of Conn.

[73] Assignee: Clairol Incorporated, New York, N.Y.

[21] Appl. No.: 114,964

[22] Filed: Oct. 30, 1987

[51] Int. Cl.$^4$ .............. A61K 7/13; C07C 149/42
[52] U.S. Cl. .............................. 8/414; 8/428; 8/429; 564/341; 564/367
[58] Field of Search .............. 8/414, 428, 429; 564/305, 341, 367, 369, 440

[56] References Cited

U.S. PATENT DOCUMENTS 1,940,757 12/1933 Lehman et al. .......................... 8/404  
3,817,995 6/1974 Bugaut et al. ....................... 544/105

FOREIGN PATENT DOCUMENTS

DE3343642 6/1985 Fed. Rep. of Germany .  
DE3530338 2/1987 Fed. Rep. of Germany .  
2438045 4/1980 France .

OTHER PUBLICATIONS

Chemical Abstracts, vol 67, No. 15, 1967, Abstract No. 73555c, Lecolier et al, "New Benzimidazoles with Morphine Activity".  
Chemical Abstracts, vol. 25, No. 23, 1982, Abstract No. 199189d, Plakidin et al, "Reaction of 2,4-Disubstituted Chlorobenzenes".  
C. A. Shand et al, "The Consugated N,N′ (Polyenediylidene)Bis-Sulphenamide Chromophore", J. Chem. Res. (M) (1982, pp. 1601-1607).

Primary Examiner—Paul Lieberman  
Assistant Examiner—Christine A. Skane  
Attorney, Agent, or Firm—Sandra M. Person

[57] ABSTRACT

Novel sulfur containing nitroamino benzene dyes of formula:

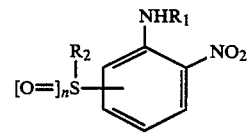

and salts thereof wherein (a) $R_1$ and $R_2$ are the same or different and are selected from the group consisting of alkyl, hydroxyalkyl, polyhydroxyalky, aminoalkyl, monoalkylamioalkyl and dialkylaminoalkyl, wherein
(b) n is 0, 1 or 2, and wherein
(c) the group

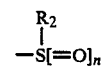

occupies a position that is meta or para to the group-$NHR_1$; a process for synthesizing these compounds and their use as direct dyeing hair dyes are being disclosed.

32 Claims, No Drawings

SULFUR-CONTAINING NITROAMINOBENZENE DYES, PROCESS AND HAIR DYE COMPOSITIONS

BACKGROUND OF THE INVENTION

This invention relates to certain novel sulfur containing nitroaminobenzene dyes and to certain processes for synthesizing such dyes. More particularly it concerns dyes of this character in which the amino group is a secondary amino group. Furthermore, this invention also relates to dyeing processes for hair that employ such dyes and compositions for carrying out these hair dyeing processes. Dyes of the aforesaid character are of the direct dye type, not requiring any oxidizing agent for color development and are generally used in semi-permanent hair coloring compositions.

Direct dyes based on nitrobenzene derivatives have been known for a long time. These have generally taken the form of mono- or disubstituted nitrobenzenes wherein the substituent groups on the nitrobenzene are amino groups, substituted amino groups or hydroxy groups of which the O and N serve as electron donor groups (See Article by John F. Corbett in Vol. 5 Chapter VII of *The Chemistry of Synthetic Dyes* by K. Venkataraman, Academic Press, New York, 1971 (pp. 508-518). In these cases, the $NO_2$ group of the nitrobenzene serves as the electron acceptor group. This system of donor and acceptor groups linked together by the unsaturated bridge that is provided by the benzene ring may serve to move the principal absorption band of the chromogen into the visible region.

INVENTION

It has now been found, quite unexpectedly, that sulfide, sulfone or sulfoxide groups bonded to a nitroaminobenzene in which the amino group is a secondary amino group provide compounds that are highly useful as direct dyes. Moreover, these new sulfur containing nitroamino dyes have proven to have a number of advantages. Although they are sulfur compounds no offensive odor has been noted from these materials as might have been expected. When applied to hair these dyes give dyeouts that range from an intense yellow to orange-yellow which renders them highly useful for blending purposes to produce naturally appearing hair colors. The present sulfur containing compounds have also been shown to have a strong affinity for hair keratin and hair dyeings made therewith possess very good wash-fastness and light-fastness properties.

PRIOR ART

Certain hydroxyethyl sulfone compounds have been disclosed in the prior art. German Offen. DE No. 3530338 describes compounds of the general formula

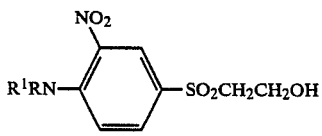

wherein R is a lower alkyl radical ($C_{1-4}$) and $R^1$ is a mono or bicyclic aryl radical. In these compounds the amino group is a tertiary amino as compared with the present invention in which the amino group is a secondary amino. This difference is significant in that the tertiary amino compounds of the type under consideration have little if any color and accordingly are not useful as direct dyes as is the case with the compounds of the present invention. Furthermore the compounds of this German reference are not disclosed as being useful as dyes much less as direct dyes as is characteristic of the compounds of this invention. The German reference compounds only said to be useful in the further manufacturing of reactive dyes.

Certain other sulfur-containing compounds have been disclosed as being useful as dye couplers or dyes. The references mentioned below are representative of such teachings. However, none of these show or would they suggest the surfur-containing nitroamino benzene dyes of this invention.

U.S. Pat. No. 1940757 (A), DE3343642 (B) and U.S. Pat. No. 3817995 (C) are of interest in disclosing compounds having the following formulas:

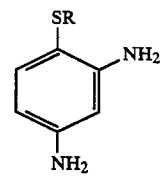

A

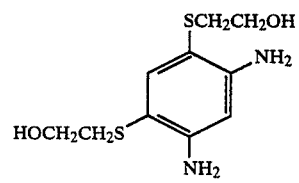

B

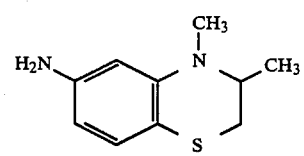

C

Greenhalgh in J. Chem. Res. (M) (1982, 1601) described the utilization of alkylthio-auxochrome (donor group) to produce intensively orange dye D (max 480 nm, max 44800).

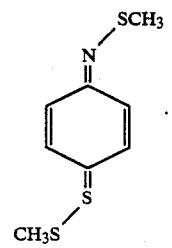

D

The application of S-dioxide (sulfone) group as an acceptor in the dye molecule can be found in blue dye such as E (French Pat. No. 2438045, 1980).

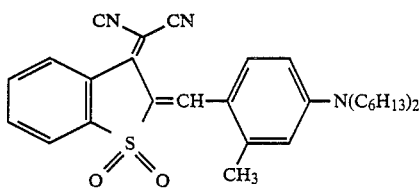

DESCRIPTION OF INVENTION

The compounds of the present invention that are of particular interest may be defined by the formula:

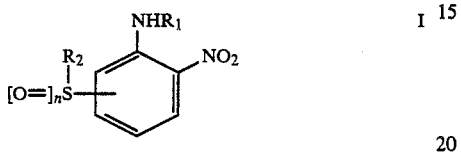

and salts thereof (e.g. tertiary amine or quaternary ammonium salts)
wherein
(a) $R_1$ and $R_2$ represent the same or different alkyl, hydroxyalkyl, polyhydroxyalkyl, aminoalkyl, mono- and dialkylaminoalkyl and
wherein
(b) n represents integer 0, 1 or 2 and
(c) the group $R_2S[=O]_n$ occupies a position that is meta or para to the group-$NHR_1$.

When n=0 in formula I above the compound is a sulfide. When n=1 or n=2, the compound is a sulfoxide or sulfone respectively. The alkyl moieties of $R_1$ and $R_2$ may be quite varied but they will ordinarily be lower alkyl moieties and preferably lower alkyl moieties having from about 1 to 4 or 6 carbons atoms. When $R_1$ or $R_2$ is a polyhydroxyalkyl group the number of hydroxy groups contained in such a radical also may vary somewhat. Generally, however, this will be from about 2 to 4 hydroxy groups.

By way of illustrating specific compounds embodied in formula I above that are useful for the present purposes the following are given. It is to be understood that this list is only illustrative of and not exhaustive of the compounds encompassed in the present invention: (3-methylamino-4-nitro)phenyl-β-hydroxyethyl sulfide; (3-methylamino-4-nitro)phenyl-β-hydroxyethyl sulfone; (3-methylamino-4-nitro)phenyl-β-dimethylaminoethyl sulfide; (3-β-hydroxyethylamino-4-nitro)phenyl-β-hydroxyethyl sulfide; (3-β-hydroxyethylamino-4-nitro)phenyl-β-hydroxyethyl sulfone; (3-β-hydroxyethylamino-4-nitro)phenyl-β-hydroxyethyl sulfoxide; (3-β,β-dimethylaminoethylamino-4-nitro)phenyl-β-hydroxyethyl sulfide; β-[N-(2-nitro-5-β-hydroxyethylmercapto)phenyl]aminoethyltrimethylammonium iodide; (β-β,γ-dihydroxypropylamino-4-nitro)phenyl-β-hydroxyethyl sulfide; (4-(β-hydroxyethylamino-3-nitro)phenyl methyl sulfone; (4-(β,γ-dihydroxypropylamino-3-nitro)phenyl methyl sulfone; (4-(dimethylaminoethylamino-3-nitro)phenyl methyl sulfone methyl iodide salt.

The process for preparing compounds of formula I above is shown by equation II below. In this equation $R_1$ and $R_2$ have the values ascribed to them above in connection with formula I and X is a halogen (e.g. F, Cl, Br, I).

Synthesis of the compounds of formula I starts from 2,4-dihalonitrobenzene (1) e.g. 2,4-difluoro- or 2,4-dichloronitrobenzene. Treatment of (1) with the amine ($R_1NH_2$) gives compound (2).

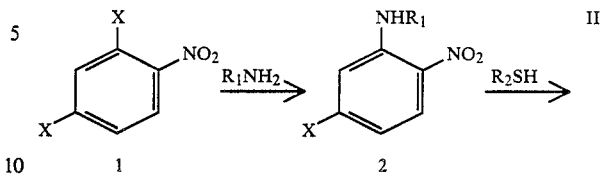

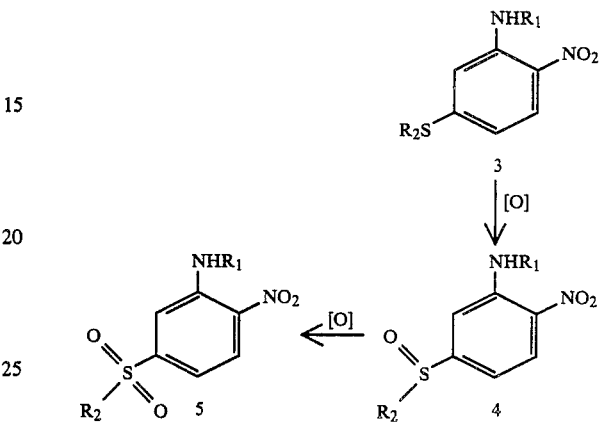

The aryl thioether (3) is prepared by aromatic nucleophilic substitution ($S_NAr$) of the compound (2) with the alkylthiol ($R_2SH$) preferably in a polar aprotic solvent such as DMSO (i.e. dimethyl sulfoxide) or DMF (i.e. dimethyl formamide). The sulfide (3) is oxidized to the sulfoxide (4) by exposure for example to 1 equivalent of sodium perborate again preferably in a polar aprotic solvent. Further oxidation of the sulfoxide (4) with an oxidizing agent such as sodium perborate results in the formation of the sulfone (5). In practice, the preparation of the sulfone (5) is carried out by treatment of the sulfide (3) with a little more than 2 equivalents of oxidant. Other reagents known to oxidize the sulfide to the sulfoxide and the sulfone (e.g. $H_2O_2$, m-chloroperbenzoic acid, a peracid etc.) can be used.

Quaternization of the compounds having a tertiary amino group is obtained by utilization of an alkyl halide (e.g. $CH_3I$).

Any of the compounds described above or any combination thereof may be employed in dyeing hair. For this purpose these compounds will ordinarily be made up into a composition (coloring composition) in which the dye compound or compounds may be conveniently applied to the head. This coloring composition will comprise a vehicle, generally an aqueous vehicle, in which the dye compound or compounds will be dissolved or otherwise distributed. The coloring composition may take any of a variety of forms. For example, it may be a simple solution of the dye compound in a solvent system, or may take the form of a cream, a gel, a lotion or aerosol composition. In each case the dye compound or compounds will be in solution or may comprisea part of an emulsion or suspension.

The quantity of dye compound or compounds of this invention that will be contained in the compositions employed herein will vary depending on the particular compound or compounds selected or the results desired. Generally, the dye compound or compounds of the present invention will constitute from about 0.05% to about 5% by weight based on the total weight of the coloring composition with the preferred concentration being from about 0.1% to about 2% on the same weight basis.

The pH of the coloring compositions of this invention may also vary somewhat. Thus, for example, this pH may be in the range of from 4 to about 12. Usually, however, the coloring compositions will be on the alkaline side with the preferred pH range being from about 8 to about 10.

Any of a variety of alkalizing agents may be used to bring the pH of the coloring compositions to its desired level. Examples of such alkalizing agents includes ammonia, monoethanolamine, diethanolamine, triethanolamine. The alkalizing agent of choice is diethanolamine.

Depending upon the form of the coloring compositions employed in this invention other adjuvants may also be employed. These will ordinarily be used to facilitate the application of the dye compound, to improve the stability of the compositions or to provide more organoleptically elegant products. Thus, for example, certain solvents may be added to the compositions to help solubilize the dyes. Similarly, surfactants, foaming agents, metal scavengers, solubilizing agents, perfumes, etc. may be utilized in the coloring compositions of this invention.

The present coloring compositions may be applied to hair on the human head in any suitable fashion to effect the dyeing of the hair. The quantity of coloring composition applied will be sufficient to saturate the hair and will be allowed to be in contact with the hair for sufficient time to impart the desired color. The time of treatment may vary somewhat, but generally this will be for about 5 to about 60 minutes, with the preferred time span being in the range of from about 20 to about 40 minutes. The optimum time period is about 30 minutes.

The temperature at which the coloring compositions of this invention is employed may also vary. However, in the usual case this will be at temperatures that can be tolerated on the human head. Preferably, this temperature will be around ambient temperatures, or somewhat higher. A treatment temperature of 24° C. has been found to be quite adequate.

After the coloring compositions is dept in contact with the hair for sufficient time to satisfactory color the hair, the composition is rinsed from the head.

The following examples are given to further illustrate this invention. It is understood, however, that the invention is not limited thereto.

EXAMPLE 1

First Stage: Preparation of 4-fluoro-2-methylaminonitrobenzene, (7)

To stirred 2,4-difluoronitrobenzene (9.54 g., 60 mmole) was added dropwise an aqueous solution of methylamine (40 wt. %) (11.6 g) in an ice bath. The mixture was stirred for another 1 hour. The yellow precipitate was collected by filtration, washed with water and dried in vacuo to give the compound (7) as yellow crystals (6.1 g., 60%).

Second Stage: Preparation of (3-methylamino-4-nitro)phenyl-β-hydroxyethyl sulfide, (8)

A mixture of 4-fluoro-2-methylaminonitrobenzene (6.8 g., 40 mmole), 2-mercaptoethanol (3.75 g., 48 mmole) and potassium carbonate (6.64 g., 48 mmole) in DMSO (20 ml) was stirred at 80° C. for 1 hour and poured into crushed ice. The product was extracted with ethyl acetate. The organic phase was washed with water three times, dried over sodium sulfate and evaporated to give a yellow solid. Recrystallization of the crude product from ethyl acetate gave 6.1 g., (67%) of the compound (8) (m.p. 91°-93° C.).

Third Stage: Preparation of (3-methylamino-4-nitro)phenyl-β-hydroxyethyl sulfone, (9)

A mixture of (3-methylamino-4-nitro)phenyl-β-hydroxyethyl sulfide (1.4 g., 6 mmole) and sodium perborate tetrahydrate (1.85 g., 12 mmole) in acetic acid (10 ml) was stirred at 85° C. for 2 hours and poured into crushed ice. The product was extracted with ethyl acetate. The organic extract was successively washed with saturated sodium bicarbonate solution, water and brine. Removal of the solvent gave the compound (9) (1.2 g., 75%) as an orange-yellow solid (m.p. 141°-142° C.).

Preparation of (3-methylamino-4-nitro)phenyl-β-dimethylaminoethyl sulfide, (10)

A mixture of 4-fluoro-2-methylaminonitrobenzene (3.4 g., 20 mmole) 2-dimethylaminoethanethiol hydrochloride (3.4 g., 24 mmole) and triethylamine (6.7 ml) in DMSO (15 ml) was stirred at 90° C. for 1 hour and poured into crushed ice. The product was extracted with ethyl acetate. The organic phase was washed with water and brine, dried over sodium sulfate and evaporated under reduced pressure. The residue was chromatographed on a silica gel column eluting with CH$_2$Cl$_2$/MeOH (20:1) to yield the sulfide (10) as an

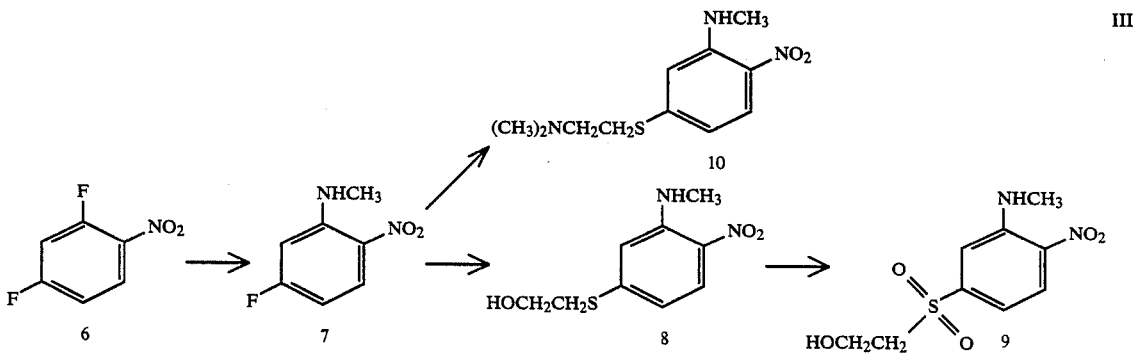

orange-yellow syrup (3.9 g., 76%) which solidified on standing (m.p. 54°-55° C.).

EXAMPLE 2

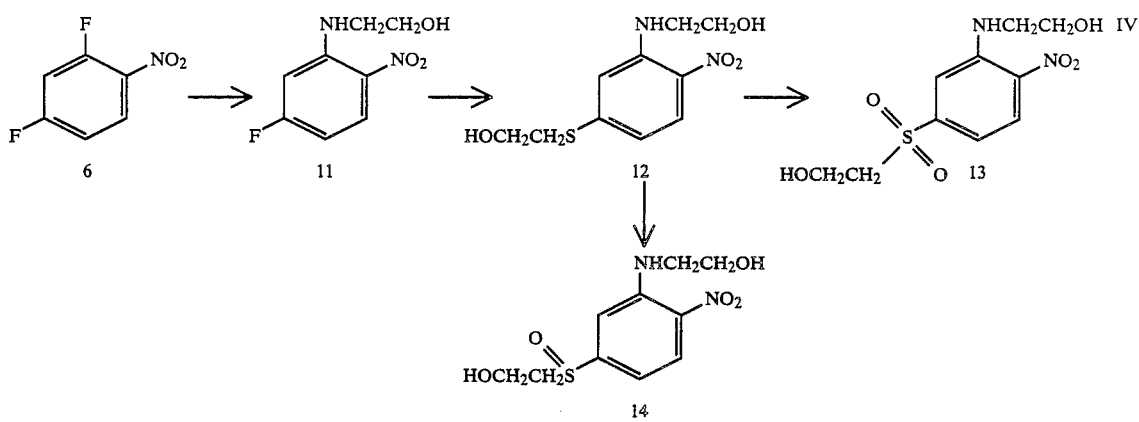

First Stage: Preparation of 4-fluoro-2-(β-hydroxyethyl)aminonitrobenzene, (11)

A mixture of 2,4-difluoronitrobenzene (6.36 g., 40 mmole), ethanolamine (3.04 g., 50 mmole) and calcium carbonate (4 g., 40 mmole) in dioxane (40 ml) was stirred at 80° C. for 1 hour and filtered while hot. The filtrate was diluted with ethyl acetate and washed with $H_2O$ and brine. The organic phase was dried over sodium sulfate and evaporated to give a reddish orange solid. Recrystallization from ethyl acetate gave the compound (11) as reddish orange crystals (5.3 g, 66%).

Second Stage: Preparation of (3-β-hydroxyethylamino-4-nitro)phenyl-β-hydroxyethyl sulfide, (12)

A mixture of 4-fluoro-2-(β-hydroxyethyl)aminonitrobenzene (2.0 g., 10 mmole), 2-mercaptoethanol (0.938 g., 12 mmole) in DMSO (6 ml) was stirred at 85° C. for 1 hour and poured into crushed ice to precipitate the crude product as a yellow crystal. The crude compound was purified by a silica gel column chromatography eluting with $CH_2Cl_2$/MeOH (20:1) to give the compound (12) (2.4 g., 93%) m.p. 99°-100° C.).

Third Stage: Preparation of (3-β-hydroxyethylamino-4-nitro)phenyl-β-hydroxyethyl sulfone, (13)

A mixture of (3-β-hydroxyethylamino-4-nitro)phenyl-β-hydroxyethyl sulfide (1.2 g., 5 mmole) and sodium perborate tetrahydrate (1.53 g., 10 mmole) in acetic acid (7 ml) was stirred at 80° C. for 1 hour. After addition of additional sodium perborate tetrahydrate (0.5 g), the mixture was stirred for another 20 min. and poured into crushed ice. The orange-yellow product precipitated was extracted with ethyl acetate, washed with saturated sodium bicarbonate solution, watr, and brine. The organic phase was dried over sodium sulfate and evaporated under reduced pressure to give the sulfone (13) (1.2 g., 83%) (m.p. 140°-143° C.).

Preparation of (3-β-hydroxyethylamino-4-nitro)phenyl-β-hydroxyethyl sulfoxide, (14).

A mixture of (3-β-hydroxyethylamino-4-nitro)phenyl-β-hydroxyethyl sulfide (1.29 g., 5 mmole) and sodium perborate tetrahydrate (0.846 g., 5.5 mmole) was stirred at 23° C. for 5 hours and poured into crushed ice. The product was extracted with ethyl acetate twice. The combined organic phases were washed with water and brine, dried over sodium sulfate and evaporated under reduced pressure. The residue was chromatographed on a silica gel column eluting with $CH_2Cl_2$/MeOH (20:1) to give the sulfoxide (14) (0.8 g., 58%) as an orange solid (m.p. 130°-132° C.).

EXAMPLE 3

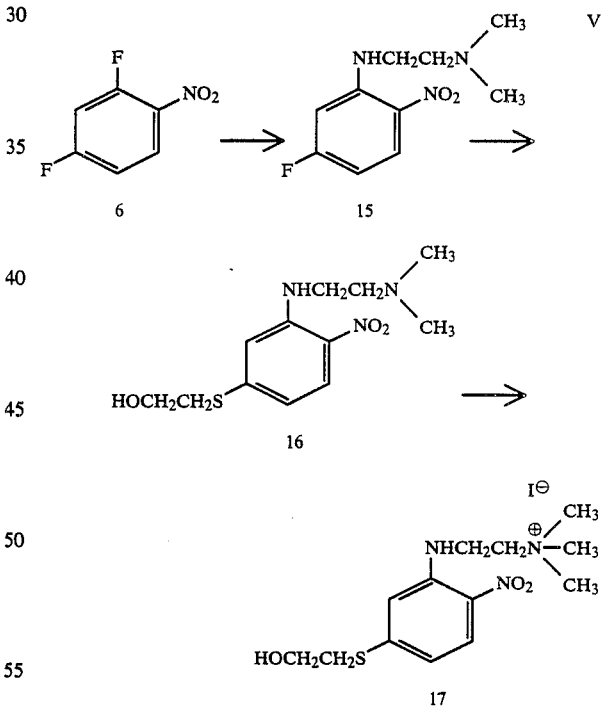

First Stage: 2-(β-dimethylaminoethyl)amino-4-fluoronitrobenzene, (15)

To a stirred solution of 2,4-difluoronitrobenzene (3.18 g., 20 mmole) In DMSO (5 ml) was added portion-wise N,N-dimethylethylene-diamine (3.52 g., 40 mmole). The mixture was stirred at 23° C. for 1 hour and poured into crushed ice. Ethyl acetate (200 ml) was added to dissolve the orange-yellow solid. The organic phase separated was washed with water and brine, dried over sodium sulfate and evaporated under reduced pressure. The residue was chromatographed on a silica gel column eluting with CH$_2$Cl$_2$/MeOH (20:1) to afford the compound (15) (2.8 g., 62%) which solidified on standing.

Second Stage:
3-(β-dimethylaminoethylamino-4-nitro)phenyl-β-hydroxyethyl sulfide, (16) A mixture of solution of 2-(β-dimethylaminoethyl)amino-4-fluoronitrobenzene (2.27 g., 10 mmole), 2-mercaptoethanol (0.94 g., 12 mmole) and potassium carbonate (1.66 g., 12 mmole) in DMSO (10 ml) was stirred at 100° C. for 0.5 hour, filtered and washed with ethyl acetate. The combined filtrate was washed with water and brine, dried over sodium sulfate and evaporated under reduced pressure.

The residue was chromatographed on a silica gel column eluting with CH$_2$Cl$_2$/MeOH (15:1) to give the sulfide (16) (2.55 g., 89% as an orange-yellow syrup.

Third Stage:
β-[N-(2-nitro-5-β-hydroxyethylmercapto)phenyl-]aminoethyl trimethylammonium iodide, (17)

A mixture of (3-β-dimethylaminoethylamino-4-nitro)phenyl-β-hydroxyethyl sulfide (2.1 g., 7.4 mmole) and methyl iodide (10 ml) was stirred at 23° C. for 1 hour. After addition to anhydrous diethyl ether, the yellow solid was collected by filtration and washed with ether to give the quaternary salt (17) (2.8 g., 89%) as yellow solid (m.p. 230°–234° C.).

EXAMPLE 4

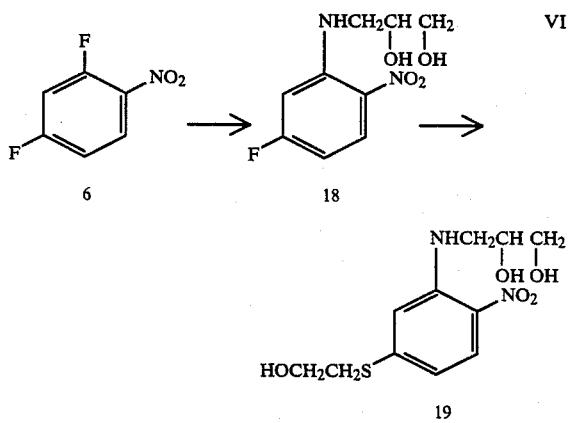

First Stage: Preparation of 2-(β,γ-dihydroxypropyl)amino-4-fluoronitrobenzene, (18)

To a stirred solution of 2,4-difluoronitrobenzene (3.18 g., 20 mmole) in DMSO (10 ml) was added portion-wise a solution of 3-amino-1,2-propanediol (3.64 g., 40 mmole) in DMSO (5 ml) in an ice bath. The mixture was stirred at 23° C. for 30 min. and poured into crushed ice. After addition of ethyl acetate, the organic layer was separated, washed with water, dried over sodium sulfate and evaporated under reduced pressure to give the compound (18) (3.6 g., 78%) as a yellow solid.

Second Stage: Preparation of 3-(β,γ-dihydroxypropylamino-4-nitro)phenyl-β-hydroxyethyl sulfide, (19)

A mixture of 2-(β,γ-dihydroxypropyl)amino-4-fluoronitrobenzene, (2.3 g., 10 mmole), mercaptoethanol (0.936 g., 12 mmole) and potassium carbonate (1.66 g., 12 mmole) in DMSO (10 ml) was stirred at 85° C. for 1 hour and poured into crushed ice. The product was extracted with ethyl acetate twice. The combined organic layers were dried over sodium sulfate and evaporated under reduced pressure. The oily residue was crystallized in ethyl acetate to give the sulfide (19) (2.5 g., 87%) as an orange yellow crystal (m.p. 102°–105° C.).

EXAMPLE 5

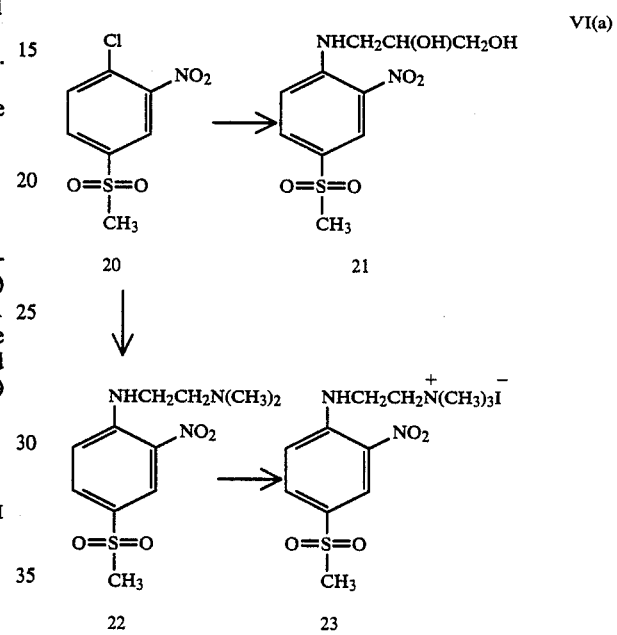

Preparation of 4-(β,γ-dihydroxypropyl)amino-3-nitrophenyl methyl sulfone, (21)

A mixture of 4-chloro-3-nitrophenyl methyl sulfone (5 g, 21 mmole) and 3-amino-1,2-propanediol (4.25 g, 47 mmole) in DMSO (15 ml) was stirred at 23° C. for 30 min. and poured into crushed ice. The resulting yellow crystal was collected by filtration and washed with ice-cold water to give the compound (21) (5.2 g, 95%) (m.p. 133° C.).

First Stage:
4-(β-dimethylaminoethyl)amino-3-nitrophenyl methyl sulfone, (22)

A mixture of 4-chloro-3-nitrophenyl methyl sulfone (4 g, 17 mmole) and N,N-dimethylethylenediamine (3.3 g, 37 mmole) in DMSO (20 ml) was stored at 75° C. for 1 hour and poured into crushed ice. The yellow solid precipitate was collected by filtration and was dissolved in ethyl acetate. The organic phase was washed with water-brine mixture twice and brine, dried over sodium sulfate, and evaporated under reduced pressure to give the sulfone (22) (3.8 g, 78%) as a yellow solid. A pure sample (m.p. 130°–131° C.) was obtained by recrystallization from ethyl acetate.

Second Stage: Methyliodide salt of 4-(β-dimethylaminoethyl)amino-3-nitrophenyl methyl sulfone, (23)

A mixture of 4-(β-dimethylaminoethyl)amino-3-nitrophenyl methyl sulfone (3.8 g, 13 mmole) and methyl iodide (10 ml) was stirred at 24° C. for 1 hour. After addition of anhydrous diethyl ether, the yellow solid was collected by filtration and washed with ether to give the quaternary salt (23) (5.68 g, 100%) as yellow solid (m.p. 254° C.).

A series of dye compositions containing compounds 8, 12, 13, 14, 17 and 19, respectively, as prepared and described were formulated. The formula for these compositions were as follows:

| | |
|---|---|
| Dye | 0.25 g |
| PEG-50 Tallow Amide | 2.0 g |
| Lauramide DEA | 1.5 g |
| Diethylene glycol monoethyl ether | 4.0 g |
| Diethanolamine | 2.0 g |
| Water | 90.25 g |

Bleached or blended gray hair samples were saturated with each of the aforesaid dye composition respectively and were left in contact with said composition for 30 minutes at 24° C. After rinsing, these dyes colored the hair samples yellow.

The light-fastness of hair samples dyes as described above with compositions containing compounds 8, 12 and 19 also described above were tested. Dyed bleached hair samples (b) and dyed blended gray hair samples (g) were tested in this manner, the samples being given a 10 hour exposure in a Fade-ometer. The Hunter Tristimuls values were recorded for each of the dyed samples before and after exposure to light in the Fade-ometer.

The results of these tests are summarized in Table I below.

TABLE I

Photostability of nitro dyes on bleached (b) and blended gray (g) hair (10 hour exposure to Fade-ometer).

| Compounds | Hair Type | Before Exposure L | a | b | After Exposure L | a | b | ΔL |
|---|---|---|---|---|---|---|---|---|
| 8 | b | 52.62 | 0.65 | 34.36 | 51.46 | 1.12 | 33.01 | 1.16 |
|   | g | 33.06 | −3.46 | 16.35 | 32.45 | −2.53 | 13.61 | 0.61 |
| 12 | b | 51.44 | 2.54 | 34.10 | 49.47 | 3.08 | 32.59 | 1.97 |
|   | g | 30.88 | −2.83 | 15.73 | 30.35 | −2.09 | 13.70 | 0.53 |
| 19 | b | 51.61 | 4.24 | 33.78 | 45.62 | 3.06 | 29.46 | 5.99 |
|   | g | 32.49 | −2.84 | 16.68 | 31.67 | 1.86 | 14.42 | 0.82 |

Three of the values were obtained with the Hunter Tristimulus Colorimeter. These are the L, a and b which are defined as:
L = brightness or total reflectance of the sample
a = degree of redness or greeness in the sample +a = red  −a = green
b = degree of yellowness of blueness in the sample +b = yellow  −b = blue
ΔL = L (before exposure) − L (after exposure)
ΔL value is the change in reflectance observed by substracting the exposed value from the unexposed value. As can be seen from Table I, ΔL value is generally very small. This represents the light stability of the dye-out. The a and b value changes indicate that the yellow shades obtained tend to change to red and blue region.

What is claimed is:

1. A compound having the formula

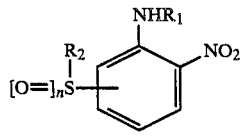

and salts thereof, wherein (a) $R_1$ and $R_2$ are the same or different and are selected from the group consisting of alkyl, hydroxyalkyl, polyhydroxyalkyl, aminoalkyl, and monoalkylaminoalkyl;

(b) n is 0, 1 or 2; and (c) the group $—S[=O]_n$ occupies a position that is meta or para to the group $NHR_1$.

2. A compound according to claim 1 wherein the group $—S[=O]_n$ has the value —S.

3. A compound according to claim 1 wherein the group $—S[=O]_n$ has the value of —S=O.

4. A compound according to claim 1 wherein the group $—S[=O]_n$ has the value

5. A compound according claims 1, 2, 3 or 4 wherein the alkyl moieties of $R_1$ and $R_2$ are lower alkyl moieties, and when $R_1$ or $R_2$ is polyhydroxyalkyl group it contains 2 to 4 hydroxy groups.

6. A compound according to claims 1, 2, 3 or 4 wherein the group $—S[=O]_n$ is meta to the group $—NHR_1$.

7. A compound according to claims 1, 2, 3 or 4 wherein the group $—S[=O]_n$ is para to the group $—NHR_1$.

8. (3-methylamino-4-nitro)phenyl-β-hydroxyethyl sulfide.

9. (3-methylamino-4-nitro)phenyl-β-hydroxyethyl sulfone.

10. (3-methylamino-4-nitro)phenyl-β-dimethylaminoethyl sulfide.

11. (3-β-hydroxyethylamino-4-nitro)phenyl-β-hydroxyethyl sulfide.

12. (3-β-hydroxyethylamino-4-nitro)phenyl-β-hydroxyethyl sulfone.

13. (3-β-hydroxyethylamino-4-nitro)phenyl-β-dimethylaminoethyl sulfoxide.

14. (3-β-dimethylaminoethylamino-4-nitro)phenyl-β-hydroxyethyl sulfide or salts thereof.

15. β-[N-(2-nitro-5-β-hydroxyethylmercapto)phenyl]aminoethyl trimethylammonium iodide or trimethylammonium sulfate salts.

16. (3-β,γ-dihydroxypropylamino-4-nitro)phenyl-β-hydroxyethyl sulfide.

17. 4-(β-hydroxyethylamino-3-nitro)phenyl methyl sulfone.

18. 4-(β,γ-dihydroxypropylamino-3-nitro)phenyl methyl sulfone.

19. 4-(dimethylaminoethylamino-3-nitro)phenyl methyl sulfone or salts thereof.

20. A process for preparing a sulfide of formula.

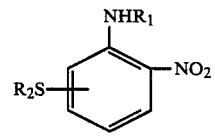

which comprises reacting a compound of formula

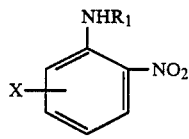

with a mercaptan of formula $R_2SH$ wherein X is a halogen and occupies a position which is meta or para to the group $NHR_1$ and $R_1$ and $R_2$ are the same or different and are selected from the group containing a alkyl, hydroxyalkyl, polyhydroxyalkyl, aminoalkyl and monoalkylaminoalkyl.

21. A process according to claim 20 including the additional step of converting compound VIII to the corresponding tertiary amine or quaternary ammonium salt.

22. A process for preparing a sulfoxide of formula

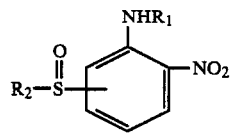

which comprises reacting a sulfide of formula

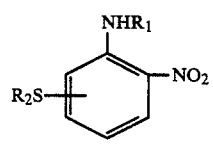

with an oxidizing agent, the molar ratio the sulfide of formula VII to oxidizing agent being such as to convert the sulfide of formula VII to the sulfoxide of formula IX, wherein $R_1$ and $R_2$ are the same or different and are selected from the group consisting of alkyl, hydroxyalkyl, polyhydroxyalkyl, aminoalkyl and monoalkylaminoalkyl; and the group $R_2S$ occupies a position which is meta or para to the group $NHR_1$.

23. A process according to claim 22 including the further step of converting the sulfoxide of formula IX to the corresponding tertiary amine or quaternary ammonium salt.

24. A process for preparing a sulfone or formula

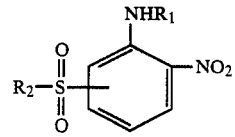

which comprises reacting a sulfide of formula

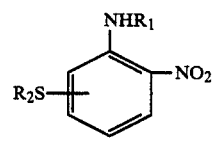

with an oxidizing agent, the molar ratio of the sulfide of formula VII to oxidizing agent being such as to convert the sulfide of formula VII to the sulfoxide of formula X, wherein $R_1$ and $R_2$ are the same different and are selected from the group consisting of alkyl, hydroxyalkyl, polyhydroxyalkyl, aminoalkyl and monoalkylaminoalkyl; and the group $R_2S$ occupies a position which is meta or para to the group $NHR_1$.

25. A process according to claim 24 including the further step of converting the sulfone of formula X to the corresponding tertiary amine or quaternary ammonium salt.

26. A composition for dyeing hair comprising a hair dye vehicle having incorporated therein an effective hair dyeing amount of a compound defined in claims 1, 2, 3 or 4.

27. A processing for dyeing hair which comprising applying to said hair a composition comprising a hair dye vehicle having incorporated therein an effective hair dyeing amount of a compound defined in claims 1, 2, 3 or 4 for sufficient time to dye said hair.

28. A compound having the formula

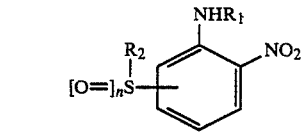

and salts thereof, wherein
(a) $R_1$ and $R_2$ are the same or different and are selected from the group consisting of: alkyl, hydroxyalkyl, polyhydroxyalkyl, aminoalkyl, monoalkylaminoalkyl and dialkylaminoalkyl;
(b) n is 0 or 1; and
(c) the group $-S[=O]_n$ occupies a position that is meta or para to the group $NHR_1$.

29. The compound of claim 28 wherein n is 0.
30. The compound of claim 28 wherein n is 1.
31. The compound of claim 28, 29 or 30 wherein $-S[=O]_n$ is meta to the $-NHR_1$ group.
32. The compound of claim 28, 29 or 30 wherein $-S[=O]_n$ is para to the $-NHR_1$ group.

* * * * *